US006544795B1

(12) United States Patent
Carnahan

(10) Patent No.: US 6,544,795 B1
(45) Date of Patent: Apr. 8, 2003

(54) METHOD AND APPARATUS FOR RAPID DETERMINATION OF FRIES REARRANGEMENT PRODUCTS IN AROMATIC POLYCARBONATE RESINS

(75) Inventor: James Claude Carnahan, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 69 days.

(21) Appl. No.: 09/665,766

(22) Filed: Sep. 20, 2000

(51) Int. Cl.[7] .............................................. G01N 33/00
(52) U.S. Cl. ...................... 436/128; 436/161; 436/172; 422/82.08
(58) Field of Search ................................ 436/172, 171, 436/164, 161, 128; 422/55, 59, 68.1, 70, 82.05, 82.08; 210/656

(56) References Cited

U.S. PATENT DOCUMENTS

| | | | |
|---|---|---|---|
| 3,028,365 A | | 4/1962 | Schnell et al. |
| 3,334,154 A | | 8/1967 | Kim |
| 3,522,725 A | | 8/1970 | Waters |
| 3,989,672 A | | 11/1976 | Vestergaard |
| 4,022,575 A | | 5/1977 | Hansen et al. |
| 4,131,575 A | | 12/1978 | Adelmann et al. |
| 4,945,001 A | * | 7/1990 | Gupta ........................ 428/412 |
| 5,100,802 A | | 3/1992 | Mickols |
| 5,151,748 A | | 9/1992 | Bur et al. |
| 5,223,224 A | | 6/1993 | Dremel et al. |
| 5,606,008 A | | 2/1997 | Sakashihta et al. |
| 5,840,256 A | | 11/1998 | Demers et al. |
| 5,846,396 A | | 12/1998 | Zanzucchi et al. |
| 5,854,684 A | | 12/1998 | Stabile et al. |
| 5,985,356 A | | 11/1999 | Schultz et al. |
| 6,045,671 A | | 4/2000 | Wu et al. |
| 6,166,133 A | * | 12/2000 | Catsman ...................... 525/67 |
| 6,166,804 A | | 12/2000 | Potvrailo et al. |
| 6,193,850 B1 | * | 2/2001 | Potyrailo et al. ...... 204/157.15 |
| 6,265,226 B1 | * | 7/2001 | Petro et al. ................. 422/100 |
| 6,296,771 B1 | * | 10/2001 | Miroslav .................... 210/656 |

OTHER PUBLICATIONS

"Flash Photochemical Studies of Polycarbonate and Related Model Compounds, Photodegradation vx. Photo–Fries Rearrangement", J.S. Humphrey et al., Macromolecules, vol. 6, pp. 305–314 (1973).

"Photochemistry of Bisphenol–A Based Polycarbonate: The Effect of the Matrix and early Detection of Photo–Fries Product Formation", C. E. Hoyle et al., J. Polym. Sci. A., vol. 30, pp. 1525–1533 (1992).

"Identification of Fluorescent Products Produced by the Thermal Treatment of Bisphenol–A–Based Polycarbonate", I.B. Rufus et al., J. App. Polym. Sci., vol. 51, pp. 1549–1558 (1994).

"Photochemistry and Photodegradation of Polycarbonate", S. Pankasem et al., Macromolecules, vol. 27, pp. 3773–3781 (1994.

* cited by examiner

Primary Examiner—Jill Warden
Assistant Examiner—Yelena Gakh
(74) Attorney, Agent, or Firm—Noreen C. Johnson; Christian G. Cabou

(57) ABSTRACT

A rapid analysis method for the determination of Fries rearrangement products in aromatic polycarbonate resins utilizes in-line determination of polymer concentration and in-line fluorescence detection of Fries rearrangement products. The method avoids time consuming sample preparation required by previous methods, allows for separation of interfering low molecular weight components, and is suitable for automation.

28 Claims, 4 Drawing Sheets

METHOD AND APPARATUS FOR RAPID DETERMINATION OF FRIES REARRANGEMENT PRODUCTS IN AROMATIC POLYCARBONATE RESINS

BACKGROUND OF THE INVENTION

The present invention relates to analysis of polymer resins. In particular, the invention relates to analysis of fluorescent products in aromatic polycarbonate resins.

Aromatic polycarbonates are typically synthesized by reaction of an aromatic diphenol, such as 2,2'-bis(4-hydroxyphenyl)propane (also known as bisphenol A or BPA), with derivatives of carbonic acid, such as phosgene or diphenyl carbonate, in the presence of a catalyst. See, for example, U.S. Pat. No. 3,028,365 to Schnell et al., U.S. Pat. No. 3,334,154 to Kim, U.S. Pat. No. 3,989,672 to Vestergaard, U.S. Pat. No. 4,131,575 to Adelmann et al., and U.S. Pat. No. 5,606,008 to Sakashita et al.; and Japanese Unexamined Patent Publications JP 2000-063507-A, JP 11-005837-A and JP 11-158261-A. When these polymerizations are conducted under melt polymerization conditions, the high temperatures of the reactions and the presence of intentionally added and adventitious catalysts can lead to thermal reactions that convert a portion of the aryl carbonate groups to salicylate esters. As shown below, Fries rearrangement of the linear aromatic polycarbonate I yields, initially, a substituted phenyl salicylate product II, which can then undergo polymerization by reaction of the pendant salicylate hydroxyl group with diphenyl carbonate (DPC) and BPA to yield a branched aromatic polycarbonate III.

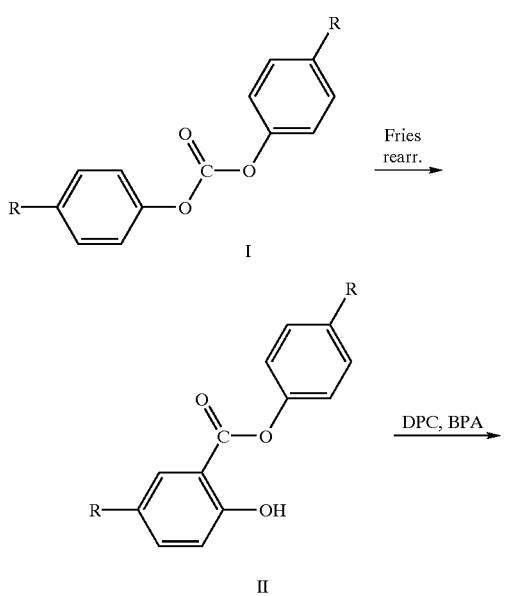

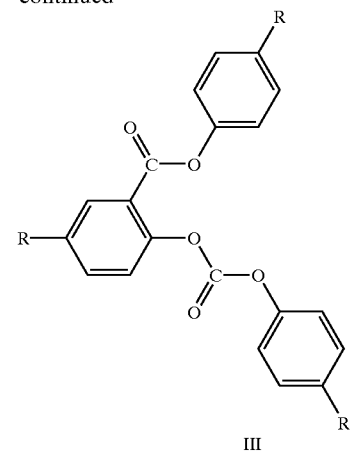

The Fries rearrangement products can also be formed photochemically, and they are observed as side products in interfacial as well as melt polymerizations. The presence of branched polycarbonate III in aromatic polycarbonate resins is generally undesirable because it leads to variations in melt behavior, color and mechanical properties. Also, the primary Fries product II can lead to darkening of the resin over time due to the long wavelength absorption of the salicylate ester moiety and oxidation of the free phenol group. It is therefore important to be able to determine the amount of Fries rearrangement products in aromatic polycarbonate resins and to discover polymerization reaction conditions that minimize the formation of Fries rearrangement products.

Traditionally, measurement of the concentration of Fries rearrangement products (where "Fries rearrangement products" refers to all salicylate-containing polymers, i.e., to the sum of the primary Fries products II and branched polycarbonates III) in aromatic polycarbonate resins has been carried out by a laborious hydrolysis of the polymer followed by high performance liquid chromatographic (HPLC) analysis of the resulting small molecules. See, for example, A. Factor, "Mechanisms of Thermal and Photodegradation of Bisphenol A Polycarbonate", Chapter 5 in R. L. Clough et al. eds., "Polymer Durability: Degradation, Stabilization, and Lifetime Prediction", 1995, American Chemical Society. Spectroscopic characterizations of Fries rearrangement products of aromatic polycarbonates have been reported in, for example, J. S. Humphrey, Jr., A. R. Shultz and D. B. G. Jaquiss, Macromolecules, vol. 6, pp. 305–314 (1973); C. E. Hoyle, H. Shah and G. L. Nelson, J. Polym. Sci. A., vol. 30, pp. 1525–1533 (1992); I. B. Rufus, H. Shah and C. E. Hoyle, J. App. Polym. Sci., vol. 51, pp. 1549–1558 (1994); and S. Pankasem, J. Kuczynski and J. K. Thomas, Macromolecules, vol. 27, pp. 3773–3781 (1994). Even when analyses were conducted spectroscopically, they involved time consuming sample preparations requiring careful weighing of polycarbonate resin and dissolution and dilution with solvent to form precise volumes of solutions having known polycarbonate concentrations. In addition, the cited spectroscopic methods have no capability to protect from interference by small contaminant molecules that may be present in the polycarbonate resin or in polymerization reaction mixtures.

When modern combinatorial methods are used to screen reaction conditions or catalyst materials, the large number of samples generated can easily overwhelm the traditional analyses described above.

There is therefore a need for an analytical method that enables rapid determination of the concentration of Fries rearrangement products in aromatic polycarbonate resins, that is free from interferences by small molecules, and that is easily automated.

BRIEF SUMMARY OF THE INVENTION

Rapid analysis of Fries product content in aromatic polycarbonate resins is provided by an analysis method comprising:

providing an analytical sample comprising an aromatic polycarbonate;

optionally, separating the analytical sample to yield a high molecular weight fraction;

performing an in-line determination of aromatic polycarbonate concentration in the analytical sample; and performing an in-line determination of the fluorescence signal due to Fries rearrangement products in the analytical sample;

wherein the total analysis time is not greater than about 5 minutes per sample.

DETAILED DESCRIPTION OF THE INVENTION

Figure 1:
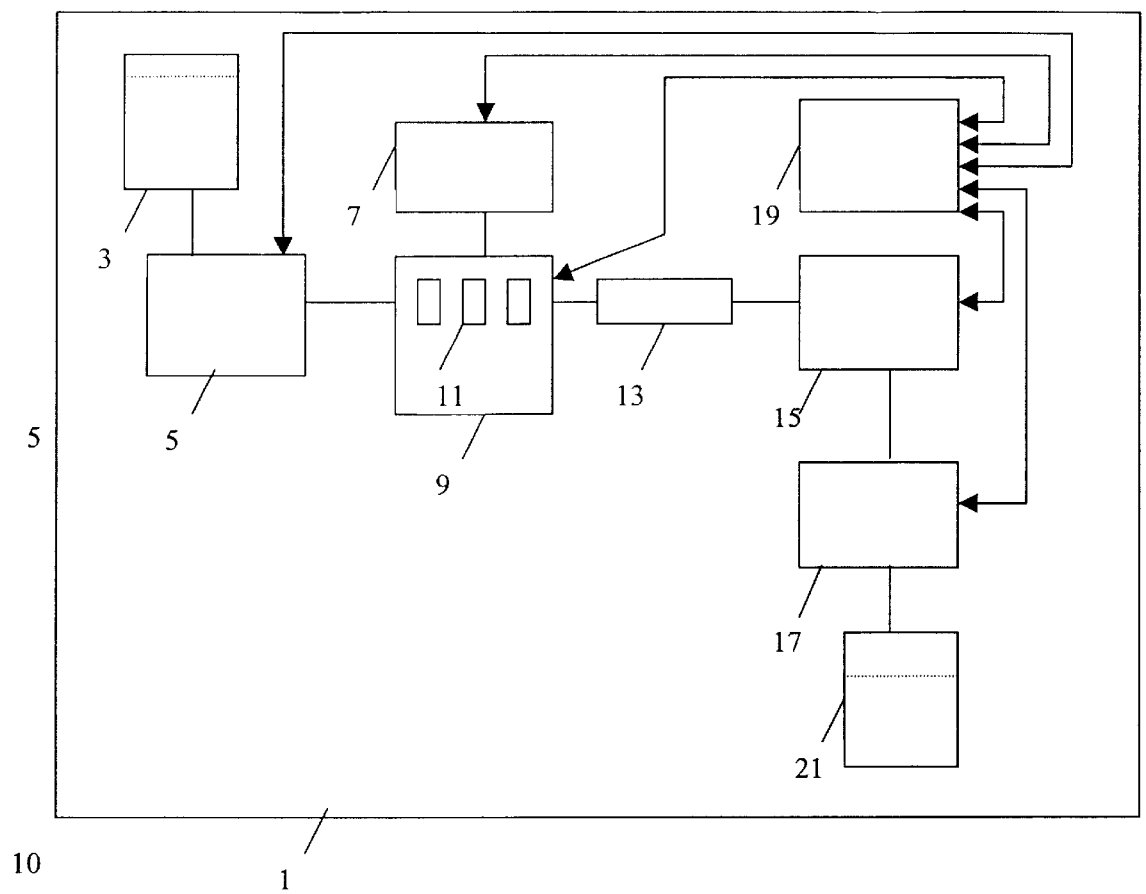
FIG. 1 is a block diagram for a system for determining the concentration of Fries rearrangement products in analytical samples comprising aromatic polycarbonate.

A method for analysis of Fries rearrangement products in aromatic polycarbonate resins comprises:

providing an analytical sample comprising an aromatic polycarbonate;

optionally, separating the analytical sample to yield a high molecular weight fraction;

performing an in-line determination of aromatic polycarbonate concentration in the analytical sample; and performing an in-line determination of the fluorescence signal due to Fries rearrangement products in the analytical sample;

wherein the total analysis time is not greater than about 5 minutes per sample.

The method may generally be considered a flow injection analysis method, or, when the method comprises separating the analytical sample to yield a high molecular weight fraction, it may be considered a liquid chromatographic method. In both flow injection analysis and liquid chromatography, a portion of an analytical sample is injected into a continuously flowing stream of carrier solvent, and one or more downstream detectors are used to characterize the sample. Flow injection analysis methods are described in, for example, U.S. Pat. No. 4,022,575 to Hansen and Ruzicka, as well as many subsequent patents which reference it. Although the term "flow injection analysis" often implies that the carrier solvent contains a reagent that reacts with at least one component of the analytical sample, we use the term in a broader sense that does not require such a reagent (for precedent for this broader sense, see, for example, in U.S. Pat. No. 5,223,224 to Dremel et al. at column 1, lines 14–27). A basic method and apparatus for liquid chromatography is described in U.S. Pat. No. 3,522,725 to J. L. Waters.

The method comprises providing an analytical sample comprising an aromatic polycarbonate. Aromatic polycarbonates are a well-known class of polymers and their preparation is described in, among many others, the patents and patent publications to Schnell and others cited in the background section, above. Aromatic polycarbonates comprise repeating units of formula IV:

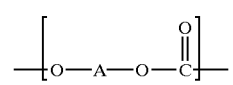

wherein A is a divalent aromatic radical derived from a dihydric phenol. The dihydric phenol employed to provide such aromatic polycarbonate polymers is a mononuclear or polynuclear aromatic compound containing as functional groups two hydroxyl radicals, each of which is attached directly to a carbon atom of an aromatic nucleus. Typical dihydric phenols include 2,2-bis-(4-hydroxyphenyl)propane (also known as bisphenol A or BPA); hydroquinone; resorcinol; 2,2-bis-(4-hydroxyphenyl)pentane; 2,4'-dihydroxydiphenylmethane; bis-(2-hydroxyphenyl)methane; bis-(4-hydroxyphenyl)methane; bis-(4-hydroxy-5-nitrophenyl)methane; 1,1-bis-(4-hydroxyphenyl)ethane; 3,3-bis-(4-hydroxyphenyl)pentane; 2,2'-dihydroxydiphenyl; 2,6-dihydroxynapthylene; bis-(4-hydroxyphenyl)sulfone; 2,2'-dihydroxydiphenylsulfone; 4,4'-dihydroxydiphenylether; and 4,4'-dihydroxy-2,5-diethoxydiphenylether. A variety of additional dihydric phenols are disclosed in U.S. Pat. No. 2,999,835 to Goldberg. It is possible to employ two or more different dihydric phenols, or a dihydric phenol in combination with a glycol, a hydroxy or acid-terminated polyester, or a dibasic acid in order to prepare a carbonate copolymer. Such carbonate copolymers are expressly encompassed by the term "aromatic polycarbonates" as used hereinafter. Preferred phenols include bis-(2-hydroxyphenyl)-methane, 1,1-bis-(4-hydroxyphenyl) ethane, 2,2-bis-(4-hydroxyphenyl)propane, and 2,2-bis-(4-hydroxyphenyl)pentane. A highly preferred phenol is 2,2-bis-(4-hydroxyphenyl)propane.

The aromatic polycarbonate may be prepared by reacting one or more hydric diphenols with a carbonate precursor.

The carbonate precursor may be, for example, phosgene or a carbonic acid diester. A preferred carbonic acid diester is diphenyl carbonate. The reaction mixture may comprise a catalyst, such as those described in, for example, Japanese Patent Publication Nos. JP 2000-063507-A, JP 11-005837-A and JP 11-158261-A.

The reaction may be conducted on the absence of solvent, under so-called melt polymerization conditions. Alternatively, the reaction mixture may comprise at least one solvent. Suitable solvents include benzene, toluene, xylene, anisole, dichlorobenzene, chlorobenzene, trichlorobenzene, tetrahydrofuran chloroform, methylene chloride, carbon tetrachloride, trichloroethylene, dichloroethane, methyl acetate, ethyl acetate, N-methylpyrrolidone, dimethylformamide, dimethylsulfoxide and mixtures comprising at least one of the foregoing solvents. Benzene, toluene, xylene, chloroform, dichloromethane, tetrahydrofuran and mixtures comprising at least one of the foregoing solvents are particularly suitable.

The analytical sample comprising an aromatic polycarbonate may be a purified polycarbonate, a polymerization reaction mixture or a polymerization reaction mixture that has been further treated. The aromatic polycarbonate may be in liquid solution or in solid form. In one embodiment, the analytical sample comprises a polymerization reaction mixture. In another embodiment, the analytical sample may be derived from a solvent-containing reaction mixture by at least partially removing solvent and other volatile components. In yet another embodiment, the analytical sample may be a solution prepared by dissolving a purified or unpurified aromatic polycarbonate resin in a suitable solvent, such as one or more of the solvents listed above for use in aromatic polycarbonate synthesis. If the analytical sample comprises a catalyst-containing polymerization reaction mixture, it is preferred that the identity and amount of catalyst are such that the catalyst does not interfere with the fluorescence measurement. In other words, it is preferred that the fluorescence excitation-emission wavelengths and intensities of the catalyst do not interfere with excitation or emission of the Fries rearrangement products. Preparation of the analytical sample comprising aromatic polycarbonate may include filtering the sample to remove particulate matter.

It is expressly contemplated to provide a plurality of analytical samples comprising aromatic polycarbonate. For example, each sample may correspond to a reaction mixture in one well of a 96-, 384-, or 1536-well plate. Such multi-well plates are well known and commercially available. The exact number of analytical samples constituting a plurality may vary widely, from two to about one million or more. For example, U.S. Pat. No. 5,854,684 to Stabile et al. describes analytical matrices comprising at least one million samples arranged in a density of at least about 10 sites per square centimeter, and U.S. Pat. No. 5,840,256 to Demers et al. provides details for a 7.25 square inch analytical matrix comprising 99,856 samples. Microscale reaction vessels and methods of delivering reagents to them are described in U.S. Pat. No. 5,846,396 to Zanzucchi et al., U.S. Pat. No. 5,985,356 to Schultz et al., and U.S. Pat. No. 6,045,671 to Wu et al.

A fixed volume of the analytical sample comprising aromatic polycarbonate is withdrawn for analysis and injected into the system, typically using a sample injector such as, for example, the Hewlett Packard model 1050 autoinjector. The analyzed portion of the analytical sample comprising aromatic polycarbonate (hereafter referred to as the injected sample) may be directly subjected to in-line determinations of aromatic polycarbonate concentration and the concentration of Fries rearrangement products. In a preferred embodiment, however, the injected sample is first separated to yield a high molecular weight fraction. This offers the advantage of removing from the analysis any small molecules whose fluorescence could interfere with fluorescence detection of Fries rearrangement products. Any chromatographic method that separates low and high molecular weight fractions may be used. Suitable methods for effecting this separation include size exclusion chromatography, normal phase liquid chromatography, reverse phase chromatography, membrane filtration, and field flow fractionation. While many commercially available size exclusion columns are suitable, a presently preferred column is the 50×7 mm 100 Angstrom column from Polymer Laboratories. When size exclusion chromatography is used to separate the high molecular weight fraction, that fraction elutes before lower molecular weight components such as diphenylcarbonate and phenol. It is expressly contemplated to employ so-called overlapping injections, so that the low molecular components of a given sample elute after the injection of the following sample but before the following sample's high molecular weight fraction elutes. This technique enables further reduction of sample analysis times.

The injected sample undergoes an in-line determination of the aromatic polycarbonate concentration in the analytical sample. This feature of the invention contributes to the speed and convenience of the method by eliminating the need for preparation of analytical samples with known aromatic polycarbonate concentrations. Suitable methods for determination of the aromatic polycarbonate concentration in the analytical sample include infrared absorption, ultraviolet absorption, differential refractive index detection, ultrasonic detection, and viscometry and evaporative light scattering detection. Detectors for each of these methods are commercially available. A presently preferred concentration detection method is differential refractive index (DRI) detection. Suitable DRI detectors include, for example, the HP 1037A differential refractive index detector available from Hewlett Packard, now Agilent Technologies. Raw data from the in-line determination of aromatic polycarbonate concentration correspond to a series of (x,y) points where x is the elapsed time since injection and y is the detector response. A plot of these points forms a chromatogram, and a baseline-to-baseline integration of the peak of interest yields an area that is directly proportional to the polymer concentration. In practice, analytical samples containing known aromatic polycarbonate concentrations may be analyzed in a calibration experiment to derive the linear function that relates peak area to aromatic polycarbonate concentration.

The injected sample also undergoes an in-line determination of the fluorescence signal due to Fries rearrangement products in the analytical sample. Suitable fluorescence detectors comprise a light source with a filter or monochromator to select the illumination wavelength for fluorescence excitation and a detector preceded by an appropriate filter or monochromator to select the wavelength for fluorescence emission. A variety of commercially available fluorescence detectors are suitable for this determination. Alternatively, a detector may be constructed including a suitable light source, an excitation wavelength selector (e.g., a monochromator or one or more filters), a flow cell, and a fluorescence emission detector that substantially excludes excitation light. A laser light source may be employed in place of the combination of a broad band light source and an excitation wavelength selector. A presently preferred detector is the HP 1046A fluorescence detector available from Hewlett Packard, now Agilent Technologies.

The selection of fluorescence excitation and emission wavelengths will depend on the wavelengths of maximum excitation and emission associated with the salicylate moiety of the Fries rearrangement products, which in turn depend on the dihydric phenol from which the aromatic polycarbonate was synthesized and the identity of the solvent used to dissolve the polycarbonate resin. In practice, it is often useful to determine the fluorescence excitation maximum and the emission maximum wavelengths using an authentic sample of the Fries rearrangement products or a model compound that is structurally similar to the Fries rearrangement products of the aromatic polycarbonate analyzed. Note that while the fluorescence emission spectrum of the Fries rearrangement products may exhibit multiple fluorescence emission maxima, for the purposes of this method, "fluorescence emission maximum" in the discussion below generally refers to the most bathochromic emission maximum, which usually falls in the range 400–650 nanometers (nm). Likewise, the term "fluorescence excitation maximum" as used below refers to the excitation maximum corresponding to the most bathochromic emission maximum. Methods to determine the fluorescence excitation maximum and the emission maximum wavelengths are well known and include excitation-emission mapping, which is described in, for example, J. R. Lakowicz, *Principles of Fluorescence Spectroscopy, Second Edition.*", Kluwer Academic/Plenum Publishers: New York, N.Y., 1999; and Ingle, J. D., Jr.; Crouch, S. R. *Spectrochemical Analysis;* Prentice Hall: Englewood Cliffs, N.J., 1988. It is generally desirable for the in-line fluorescence determination of the concentration of Fries rearrangement products to use an excitation wavelength within about 30 nm of the fluorescence excitation maximum, preferably within about 20 nm of the fluorescence excitation maximum, more preferably within about 10 nm of the fluorescence excitation maximum. In some cases it may be desirable to use an excitation wavelength displaced from the maximum excitation wavelength by as much as 30 nm to avoid excitation of an interfering emission from the aromatic polycarbonate. It is generally desirable for the in-line fluorescence determination of the concentration of Fries rearrangement products to use an emission wavelength within about 50 nm of the fluorescence emission maximum, preferably within about 30 nm of the fluorescence emission maximum, more preferably within about 10 nm of the fluorescence excitation maximum. In some cases it may be desirable to use an excitation wavelength displaced from the maximum excitation wavelength by as much as 50 nm to avoid an interfering emission from the aromatic polycarbonate.

For example, selective detection of Fries rearrangement products in aromatic polycarbonate derived from bisphenol A (i.e., BPA-PC), where the analytical sample containing BPA-PC is analyzed in chloroform, the detector may suitably employ excitation wavelengths of about 280 to about 340 nm, with wavelengths of about 290 to about 330 nm being preferred, and wavelengths of about 300 to about 330 nm being more preferred. The fluorescence detector may suitably detect fluorescence emission wavelengths of about 420 nm to about 600 nm, with wavelengths of about 440 nm to about 500 nm being preferred, and wavelengths of about 450 nm to about 470 nm being more preferred.

Raw data from the in-line determination of the concentration of Fries rearrangement products correspond to a series of (x,y) points where x is the elapsed time since injection and y is the fluorescence emission detector response. A plot of these points forms a chromatogram, and a baseline-to-baseline integration of the peak of interest yields an area that is directly proportional to the concentration of Fries rearrangement products. As for the aromatic polycarbonate concentration determination, a calibration experiment may be used to determine the linear function relating detector response (peak area) to sample concentration. For the determination of the concentration of Fries rearrangement products, the calibration experiment may employ analytical samples containing known concentrations of a polycarbonate Fries rearrangement products or a suitable model compound.

As an alternative to separately calibrating the concentration detector and fluorescence detector, as described above, both detectors may be calibrated in a single procedure. Analytical samples containing known concentrations of Fries rearrangement products may be analyzed in a calibration experiment to derive the linear function that relates fluorescence and concentration peak area ratios to Fries concentration. The linear function relates the ratio (fluorescence signal:concentration signal) to the independently determined Fries concentration in the sample. The Fries concentration may be independently determined by the known HPLC method.

The in-line determination of aromatic polycarbonate concentration and the in-line determination of the concentration of Fries rearrangement products can be conducted sequentially in either order.

A key advantage of the method is its speed. The total analysis time per sample, measured from the injection of one sample to the injection of the following sample, is not greater than 5 minutes, preferably not greater than 3 minutes, more preferably not greater than 90 seconds, yet more preferably not greater than 60 seconds, even more preferably not greater than about 40 seconds.

In a preferred embodiment, the method is automated so that preparation and analysis of a plurality of analytical samples comprising aromatic polycarbonate are prepared and analyzed without human intervention. Such automated methods may use a solvent preparation module for robotic preparation of solvent-containing analytical samples from a plurality of solid aromatic polycarbonate samples, such as samples in a combinatorial library. Methods and equipment, including commercially available equipment, for automating sample preparation and analysis are known to those of ordinary skill in the art. Equipment suppliers for applicable sample handling, dissolution and dilution automation equipment include Quadrex, Gilson, Hamilton, Zinnser, and Packard Instruments. Such automated methods for sample preparation and analysis may include the use of variable temperatures, pressures and atmospheres.

FIG. 1 shows a block diagram for an analytical system 1 for determining the concentration of Fries rearrangement products in samples comprising aromatic polycarbonate. The system comprises a solvent reservoir 3, a solvent delivery system 5 for providing a flow of solvent that carries the sample through the system 1; an (optional) sample preparation module 7 for preparing analytical sample solutions from solid aromatic polycarbonate samples; an autoinjector 9 for injecting a portion of each analytical sample 11 into the system; an (optional) chromatographic column 13 for separating the high molecular weight fraction of the analytical sample 11; a fluorescence detector 15 for detecting Fries rearrangement products; a concentration detector 17 for determining the aromatic polycarbonate concentration in the analytical sample 11; an (optional) computer 19 for calculating the concentration of Fries rearrangement products in the polycarbonate resin based on the aromatic polycarbonate concentration in the analytical sample and the concentration of Fries rearrangement products in the analytical sample, and, optionally, for responsively controlling one or more of the solvent delivery system 3, the sample preparation module 5, the autoinjector 7, the fluorescence detector 13, and the concentration detector 15; and a waste reservoir 21. Although this embodiment is not shown, the concentration detector 15 may precede the fluorescence detector 13. In a preferred embodiment, the system performs automated analyses of a plurality of analytical samples.

The invention is further illustrated by the following non-limiting examples.

EXAMPLE 1

This example demonstrates a linear correlation between Fries product concentration and fluorescence emission intensity. A Hewlett Packard (HP) model 1050 pump, an HP model 1050 autoinjector, a 50×7 mm 100 Angstrom size exclusion column from Polymer Laboratories (part number 1110-1520), an HP 1046A fluorescence detector, and an HP 1037A differential refractive index detector were connected in series. The flow rate of the chloroform solvent was 1.5 ml/min giving an analysis time of about 1.2 minutes per sample. Samples of 25 microliters containing varying known concentrations of compound V, a model for branched aromatic polycarbonate

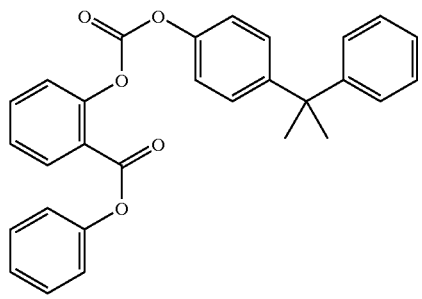

Figure 2:
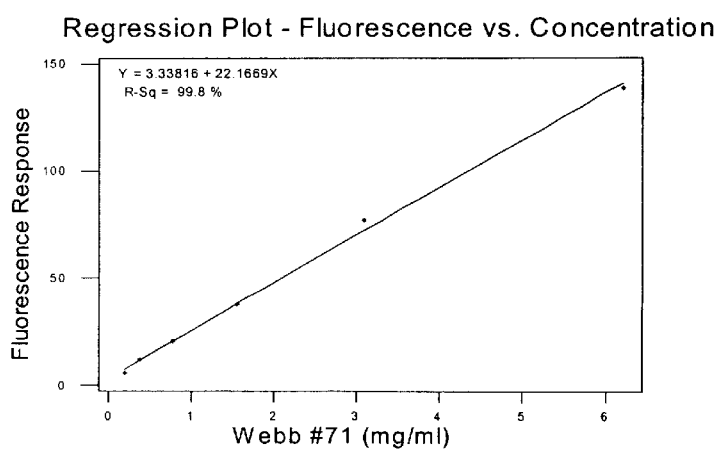
FIG. 2 is a calibration curve for fluorescence emission at 465 nm (325 nm excitation) as a function of the concentration of a model compound for Fries rearrangement products.

V synthesized from bisphenol A, were analyzed to yield fluorescence intensities at 465 nm (325 nm excitation). The results of this calibration procedure are shown in FIG. 2, which shows an excellent linear correlation between the fluorescence response and the concentration of model compound IV.

Figure 3:
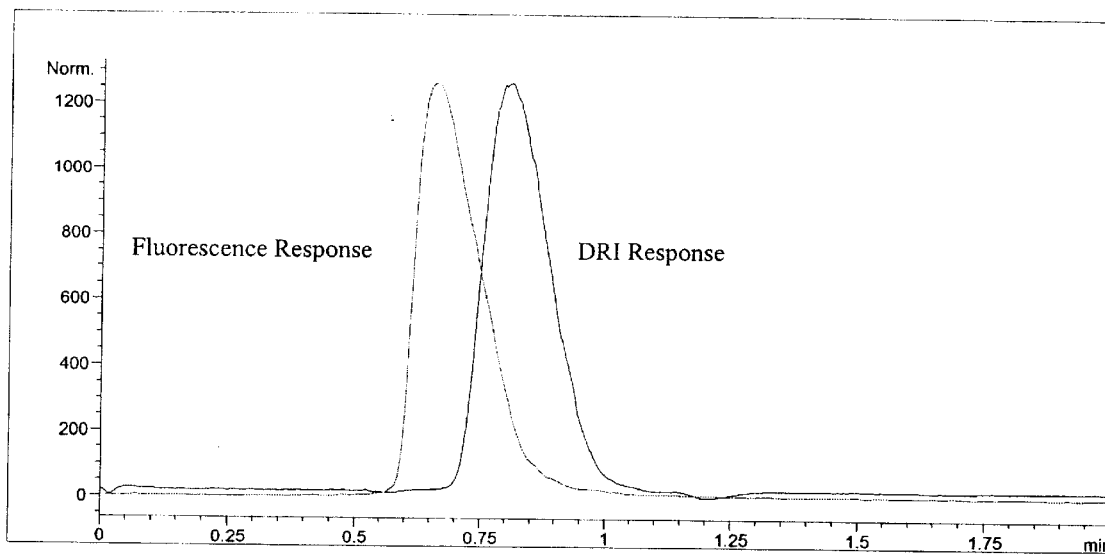
FIG. 3 overlays normalized chromatograms for fluorescence and differential refractive index detection of a melt synthesized BPA-polycarbonate resin. This material had a Fries content of 748 ppm by the HPLC method and a weight average molecular weight of 21000 Daltons by an independent GPC determination.
Figure 4:
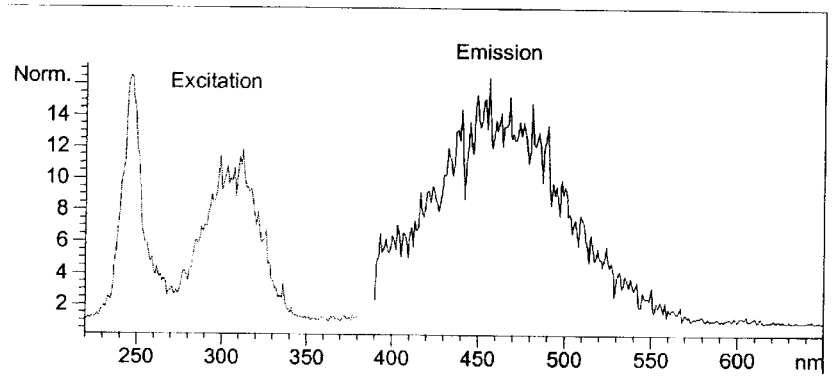
FIG. 4 shows excitation (465 nm emission) and emission (325 nm excitation) spectra for a model compound for Fries rearrangement products. The model compound was the cumylphenol carbonate of phenyl salicylate.

Typical normalized chromatograms for the fluorescence emission and differential refractive index (DRI) detectors are shown in FIG. 3. The sample was a melt polycarbonate with approximately 748 ppm of Fries as determined by the traditional hydrolysis-HPLC method. The offset in time is due to the volume of the transfer line between the detectors. The values for the concentration detector and for the fluorescence signal were determined by integration of the peak from baseline-to-baseline. Fluorescence detection was conducted with excitation at 325 and emission at 465 nm. The excitation and emission spectra of the model compound determined using a stop-flow technique in the HP 1046A detector are shown in FIG. 4. When considered in light of published spectra for aromatic polycarbonate reaction products (see, for example, S. Pankasem, J. Kuczynski and J. K. Thomas, *Macromolecules,* vol. 27, pp. 3773–3781 (1994); I. B. Rufus, H. Shah and C. E. Hoyle, J. App. Polym. Sci., vol. 51, pp. 1549–1558 (1994); and C. E. Hoyle, H. Shah and G. L. Nelson, *J. Polym. Sci. A.,* vol. 30, pp. 1525–1533 (1992)), these spectra suggest that the salicylate chromophore of the model compound has a fluorescence emission centered at about 460 nm with a corresponding excitation centered at about 310 nm. As a practical matter, utilizing an excitation wavelength longer than 310 nm (e.g., as long as 340 nm) has the advantage of reducing aromatic polycarbonate background fluorescence, which must be traded off against reduced sensitivity for the Fries product fluorescence.

EXAMPLE 2

Figure 5:
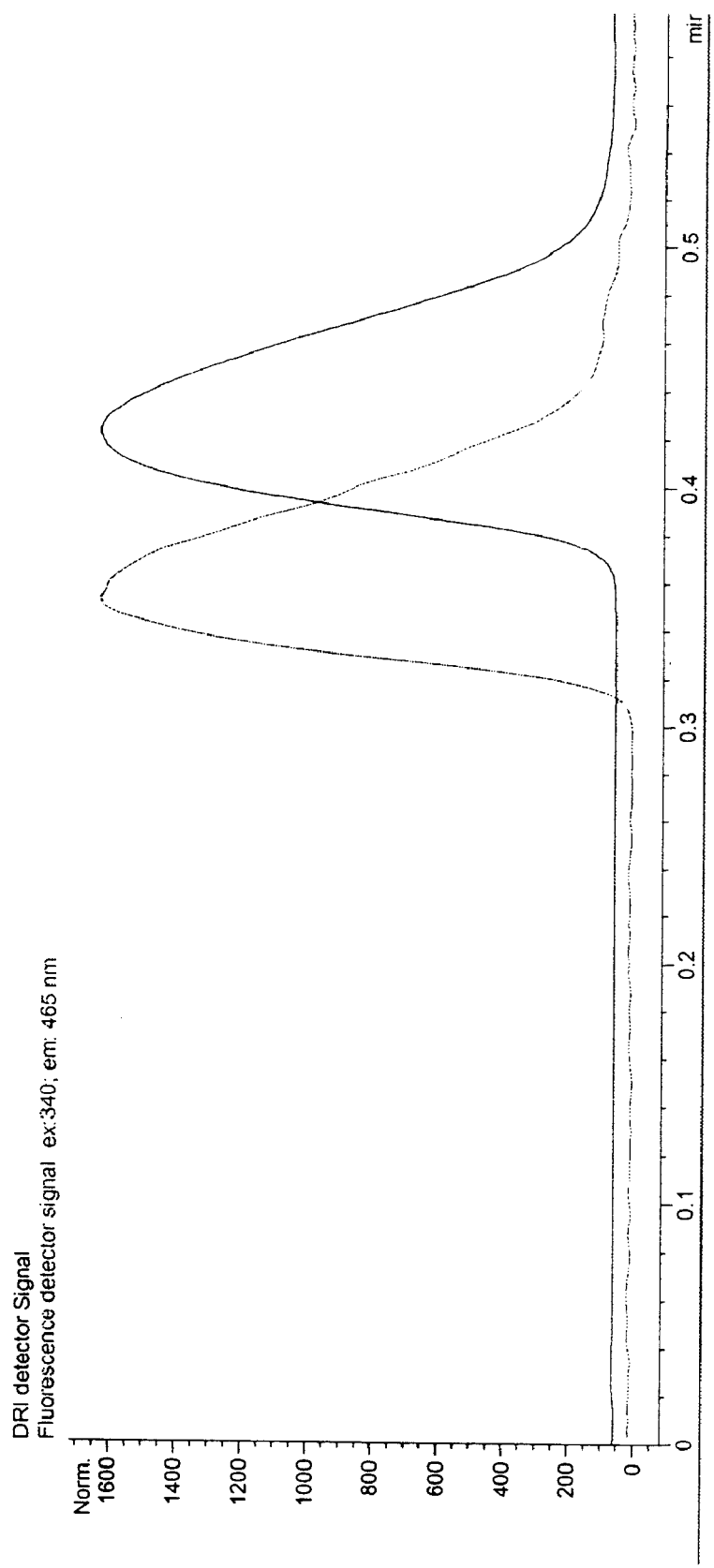
FIG. 5 overlays normalized chromatograms for fluorescence and differential refractive index detection of a melt synthesized BPA-polycarbonate resin. This material had a Fries content of 540 ppm by the HPLC method and a weight average molecular weight of 18500 Daltons by an independent GPC determination.

The procedure of Example 1 was used, except that a higher flow rate of 3.0 ml/min was utilized. The melt-synthesized polycarbonate used for this example had a Fries content of 540 ppm by the HPLC method and a weight average molecular weight of 18500 Daltons by an independent GPC determination. Fluorescence and DRI chromatograms are overlaid in FIG. 5 and demonstrate an analysis time of about 35 seconds per sample.

EXAMPLE 3

Figure 6:
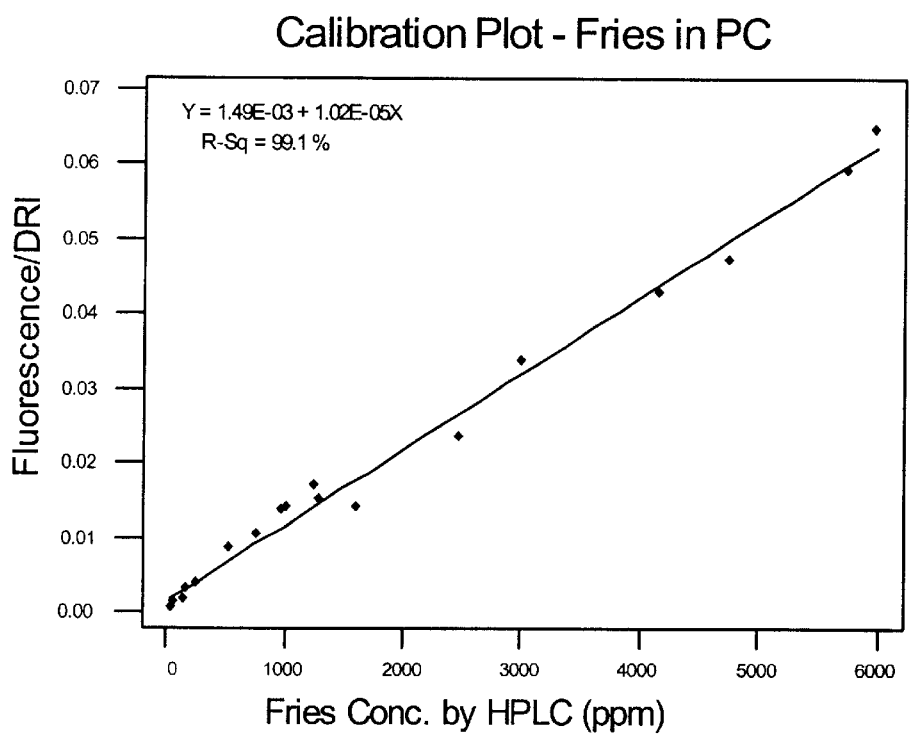
FIG. 6 is a plot of the concentration of Fries rearrangement products as determined by hydrolysis/HPLC versus the same as determined by fluorescence and differential refractive index.
Figure 7:
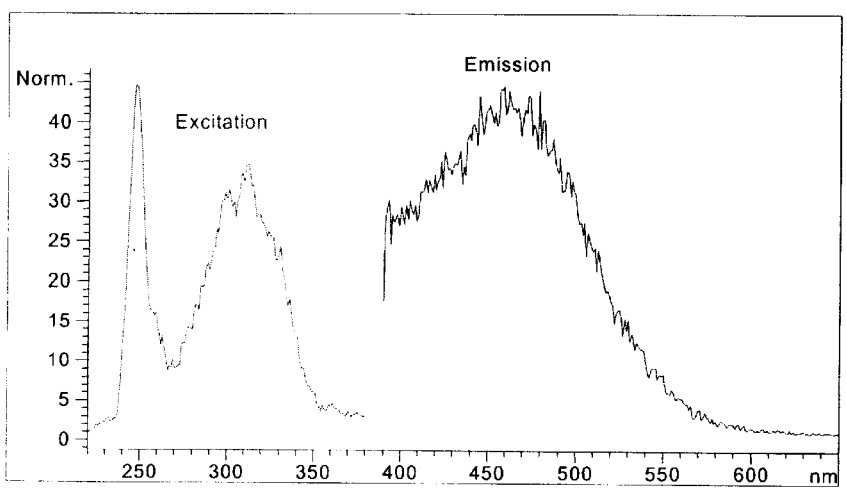
FIG. 7 shows excitation (at 465 nm emission) and emission (at 325 nm excitation) spectra for a polycarbonate sample containing Fries rearrangement products.

A series of aromatic polycarbonates prepared by melt polymerization of bisphenol A and diphenylcarbonate that had been independently analyzed using the technique of hydrolysis followed by HPLC (for a similar procedure, see A. Factor and M. L. Chu, *Polym. Degrad. Stab.,* volume 2, pages 203 ff. (1980) were analyzed with fluorescence and differential refractive index detection using the apparatus described in Example 1. Test results are plotted in FIG. 6. An excellent linear correlation was observed between the rapid fluorescence/DRI method and the laborious hydrolysis/HPLC method. Multiple runs of the same sample showed the method reproducibility to be very high with a relative standard deviation of the Fries concentration being 1.3% with a limit of detection of less than 25 parts per million (ppm). The excitation and emission spectra of one of the melt polymerization samples are shown in FIG. 7 and can be compared with the spectra in FIG. 4 for the model compound IV.

EXAMPLE 4

This example describes automated sample preparation and analysis. A 96-well microtiter plate constructed of a vitreous material is used for the reaction of bisphenol-A with diphenylcarbonate catalyzed by a series of inorganic and organic bases. The products of the polymerization reaction consist of a polymer film of between 1 and 100 milligrams in the wells of the microtiter plate. Preferably, the resulting polymer weight is in the range of 10 to 40 milligrams and more preferably in the range of 20 to 30 milligrams. The plate, after cooling from reaction temperature, is placed in a Quadra 96 Model 230 robotic liquid handling system and an aliquot of chloroform is added to all of the wells simultaneously. The well plate is covered, agitated gently to facilitate polymer dissolution and mixing, and inserted into a Gilson probe autosampler that is the sampling device for an Agilent 100 HPLC equipped with a short size exclusion column, Agilent Model 1100 UV detector, Waters Associates Model 410 differential refractive index detector and a Shimadzu 10Axl fluorescence detector. The solvent for the analysis is chloroform. The Gilson single probe autosampler removes an aliquot of the polymer solution from the 96 well plate and injects the sample into the HPLC system for analysis. The per sample analysis time for multiple analyses depends on the combination of sampling cycle time and chromatographic dwell time. Using overlapping injections, a flow rate of 3.0 mL/min, and preparation of a given sample during chromatographic analysis of the previous sample, a sample analysis time of about 20 seconds is feasible.

The above examples demonstrate rapid determination of the concentration of Fries rearrangement products in aromatic polycarbonate resins using a direct chromatographic technique that determines both the aromatic polycarbonate concentration and the fluorescence response due to the Fries rearrangement products. The method has the capability of removing interferences from small molecules that are not part of the polymer composition. The method is also amenable to automated analysis of samples derived from microtiter plates or arrays of reaction vials. Uses for the method include analysis of solid isolated aromatic polycarbonate resins, as well as analysis of a plurality of reaction mixtures constituting a combinatorial screening of aromatic polycarbonate polymerization reaction conditions.

While preferred embodiments have been shown and described, various modifications and substitutions may be made thereto without departing from the spirit and scope of the invention. In particular, the method has been demonstrated for analysis of aromatic polycarbonate samples prepared by melt synthesis, but it is suitable for analysis of polycarbonates and aromatic polyesters prepared by various means. Accordingly, it is to be understood that the present invention has been described by way of illustration and not limitation.

All cited patents and other references are incorporated herein by reference.

What is claimed is:

1. A method of determining the concentration of a Fries rearrangement product, comprising:
   conducting a reaction to produce an analytical sample comprising an aromatic polycarbonate including a Fries rearrangement product;
   injecting the analytical sample into a continuously flowing stream of carrier solvent;
   determining an aromatic polycarbonate concentration in the sample; and
   irradiating the sample to produce a fluorescence signal that is proportional to the Fries rearrangement product in the sample.

2. The method of claim 1, wherein the aromatic polycarbonate is synthesized from at least one dihydric phenol selected from the group consisting of 2,2-bis-(4-hydroxyphenyl)propane; hydroquinone; resorcinol; 2,2-bis-(4-hydroxyphenyl)pentane; 2,4'-dihydroxydiphenylmethane; bis-(2-hydroxyphenyl)methane; bis-(4-hydroxyphenyl)methane; bis-(4-hydroxy-5-nitrophenyl)methane; 1,1-bis-(4-hydroxyphenyl)ethane; 3,3-bis-(4-hydroxyphenyl)pentane; 2,2'-dihydroxydiphenyl; 2,6-dihydroxynapthylene; bis-(4-hydroxyphenyl)sulfone; 2,2'-dihydroxydiphenylsulfone; 4,4'-dihydroxydiphenylether; and 4,4'-dihydroxy-2,5-diethoxydiphenylether.

3. The method of claim 1, comprising separating a polymerization reaction mixture into said analytical sample comprising at least a higher molecular weight fraction prior to injecting the sample into the continuously flowing stream of carrier solvent.

4. The method of claim 3, wherein separating the analytical sample comprises the use of size exclusion chromatography or normal phase liquid chromatography.

5. The method of claim 1, wherein determining the polymer concentration in the analytical sample utilizes one or more detection methods selected from the group consisting of infrared absorption spectroscopy, ultraviolet absorption spectroscopy, differential refractive index detection, ultrasonic detection, viscometry, and evaporative light scattering detection.

6. The method of claim 1, wherein the sample is irradiated at an excitation wavelength selected according to the wavelength of maximum excitation associated with a salicylate moiety of the Fries rearrangement product in the sample.

7. The method of claim 1, wherein the sample is irradiated at an excitation wavelength selected according to the wavelength of maximum excitation associated with a salicylate moiety of the Fries rearrangement product and the carrier solvent.

8. The method of claim 1, wherein the sample is irradiated at an excitation wavelength determined by irradiation of an authentic sample of the Fries rearrangement product or by irradiation of a model compound that is structurally similar to the Fries rearrangement product.

9. The method of claim 1, comprising sequentially determining the aromatic polycarbonate concentration and then irradiating the sample to produce the fluorescence signal or sequentially irradiating the sample to produce the fluorescence signal and then determining the aromatic polycarbonate concentration.

10. The method of claim 1, comprising preparing an array of sample mixtures in a well plate and injecting at least one analytical sample from a well of the plate into the continuously flowing stream of carrier solvent.

11. The method of claim 1, wherein a time per sample from the injection of the sample to the injection of a following sample is not greater than 5 minutes.

12. The method of claim 1, wherein a time per sample from the injection of the sample to the injection of a following sample is not greater than 3 minutes.

13. The method of claim 1, wherein a time per sample from the injection of the sample to the injection of a following sample is not greater than 90 seconds.

14. The method of claim 1, wherein a time per sample from the injection of the sample to the injection of a following sample is not greater than 60 seconds.

15. The method of claim 1, wherein a time per sample from the injection of the sample to the injection of a following sample is not greater than 40 seconds.

16. A method of determining the concentration of a Fries rearrangement product, comprising:
   conducting a reaction to produce a polymerization reaction mixture comprising an aromatic polycarbonate including a Fries rearrangement product;
   separating the polymerization reaction mixture into an analytical sample comprising at least a higher molecular weight fraction;
   determining an aromatic polycarbonate concentration in the sample; and
   irradiating the sample to produce a fluorescence signal that is proportional to the Fries rearrangement product in the sample.

17. The method of claim 16, further comprising preparing at least one analytical sample by dissolving the separated higher molecular weight fraction in a suitable solvent to form said sample.

18. The method of claim 16, further comprising preparing at least one analytical sample by dissolving the separated higher molecular weight fraction in a suitable solvent to form said sample, wherein the solvent is selected from the group consisting of benzene, toluene, xylene, chloroform, tetrahydrofuran, methylene chloride, trichloroethylene, dichloroethane, methyl acetate, ethyl acetate and mixtures thereof.

19. The method of claim 16, wherein the aromatic polycarbonate is synthesized from at least one dihydric phenol selected from the group consisting of 2,2-bis-(4-hydroxyphenyl)propane; hydroquinone; resorcinol; 2,2-bis-(4-hydroxyphenyl)pentane; 2,4'- dihydroxydiphenylmethane; bis-(2-hydroxyphenyl)methane; bis-(4-hydroxyphenyl)methane; bis-(4-hydroxy-5-nitrophenyl)methane; 1,1-bis-(4-hydroxyphenyl)ethane; 3,3-bis-(4-hydroxyphenyl)pentane; 2,2'-dihydroxydiphenyl; 2,6-dihydroxynapthylene; bis-(4-hydroxyphenyl)sulfone; 2,2'-dihydroxydiphenylsulfone; 4,4'-dihydroxydiphenylether; and 4,4'-dihydroxy-2,5-diethoxydiphenylether.

20. The method of claim 16, wherein determining the polymer concentration in the analytical sample utilizes one or more detection methods selected from the group consisting of infrared absorption spectroscopy, ultraviolet absorption spectroscopy, differential refractive index detection, ultrasonic detection, viscometry, and evaporative light scattering detection.

21. The method of claim 16, wherein the sample is irradiated at an excitation wavelength selected according to the wavelength of maximum excitation associated with a salicylate moiety of the Fries rearrangement product in the sample.

22. The method of claim 16, wherein the sample is irradiated at an excitation wavelength selected according to the wavelength of maximum excitation associated with a salicylate moiety of the Fries rearrangement product and the carrier solvent.

23. The method of claim 16, wherein the sample is irradiated at an excitation wavelength determined by irradiation of an authentic sample of the Fries rearrangement product or by irradiation of a model compound that is structurally similar to the Fries rearrangement product.

24. The method of claim 16, comprising sequentially determining the aromatic polycarbonate concentration and then irradiating the sample to produce the fluorescence signal or sequentially irradiating the sample to produce the fluorescence signal and then determining the aromatic polycarbonate concentration.

25. The method of claim 16, comprising preparing an array of sample mixtures in a well plate and separating at least one sample mixture into an analytical sample comprising at least a higher molecular weight fraction.

26. The method of claim 16, comprising separating the polymerization reaction mixture by eluting into a first high molecular weight fraction and into a lower molecular weight fraction and commencing the eluting of a next polymerization reaction mixture before the complete eluting of the first high molecular weight fraction.

27. The method of claim 1, wherein the analytical sample is filtered to remove particulate matter.

28. The method of claim 16, wherein the polymerization reaction mixture is filtered to remove particulate matter.

* * * * *